United States Patent
Dooney, Jr.

(10) Patent No.: US 10,130,354 B2
(45) Date of Patent: Nov. 20, 2018

(54) LIMITED SLIDING SUTURE IN SUTURE ANCHOR

(71) Applicant: Arthrex, Inc., Naples, FL (US)

(72) Inventor: Thomas Dooney, Jr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 549 days.

(21) Appl. No.: 14/827,901

(22) Filed: Aug. 17, 2015

(65) Prior Publication Data

US 2017/0049431 A1 Feb. 23, 2017

(51) Int. Cl.
*A61B 17/04* (2006.01)

(52) U.S. Cl.
CPC .. *A61B 17/0401* (2013.01); *A61B 2017/0404* (2013.01); *A61B 2017/044* (2013.01); *A61B 2017/0445* (2013.01); *A61B 2017/0451* (2013.01); *A61B 2017/0464* (2013.01); *A61B 2017/0496* (2013.01)

(58) Field of Classification Search
CPC .......... A61B 17/0401; A61B 2017/044; A61B 2017/0451; A61B 2017/0496; A61B 2017/0445; A61B 2017/0464
See application file for complete search history.

(56) References Cited

U.S. PATENT DOCUMENTS

| | | | |
|---|---|---|---|
| 5,984,933 A | 11/1999 | Yoon | |
| 6,986,781 B2 | 1/2006 | Smith | |
| 8,048,157 B2 | 11/2011 | Albertorio | |
| 8,128,658 B2 * | 3/2012 | Kaiser | A61B 17/0401 606/232 |
| 8,449,612 B2 | 5/2013 | Delli-Santi et al. | |
| 8,652,171 B2 | 2/2014 | Stone et al. | |
| 8,821,542 B2 | 9/2014 | Zirps et al. | |
| 8,894,684 B2 | 11/2014 | Sengun | |
| 8,979,895 B2 | 3/2015 | Miller | |
| 9,034,014 B2 * | 5/2015 | Catania | A61B 17/0401 606/232 |
| 2002/0019649 A1 | 2/2002 | Sikora et al. | |
| 2002/0169478 A1 | 11/2002 | Schwartz et al. | |
| 2004/0138683 A1 | 7/2004 | Shelton et al. | |
| 2007/0225719 A1 * | 9/2007 | Stone | A61B 17/0401 606/232 |
| 2012/0059417 A1 * | 3/2012 | Norton | A61B 17/0401 606/232 |
| 2013/0096611 A1 | 4/2013 | Sullivan | |
| 2015/0051644 A1 | 2/2015 | Holmes, Jr. | |

FOREIGN PATENT DOCUMENTS

WO WO 2004/049958 A1 6/2004
WO WO 2005/102190 A2 11/2005

* cited by examiner

*Primary Examiner* — Anh T Dang
(74) *Attorney, Agent, or Firm* — Blank Rome LLP

(57) ABSTRACT

Tensionable systems, devices, and methods for tissue repairs. A fixation device has a post and a flexible strand which passes around the post and is provided with one stop member on one side of the post, or with two stop members, one on each side of the post. Stop members allow a flexible strand to slide around the post and become fixed for approximation of tissue to tissue and tensioning.

10 Claims, 4 Drawing Sheets

LIMITED SLIDING SUTURE IN SUTURE ANCHOR

BACKGROUND

The present disclosure relates to surgical devices and tissue repairs and, in particular, to devices for repair or fixation of soft tissue to bone with optimal suture tension.

SUMMARY

Tensionable systems, devices, and methods for tissue repairs are disclosed. A fixation device has a post and flexible strand which passes around the post and is provided with one stop member on one side of the post, or two stop members, one on each side of the post. Stop members allow a flexible strand to slide around the post and become fixed for approximation of tissue to tissue and tensioning.

A suture anchor has a body with a post, and a suture strand passing into the anchor body, around the post, and out of the anchor body. A suture strand has one or more knots or stoppers, preventing the suture strand from moving too far in one or both directions. A suture anchor allows tensioning of suture as necessary and after insertion into bone, and allows adjustment of both the tension of the suture and the location of tissue with respect to the bone. A suture anchor with a suture that has limiting sliding ability can help a user achieve optimal suture tension.

DETAILED DESCRIPTION

Figure 1:
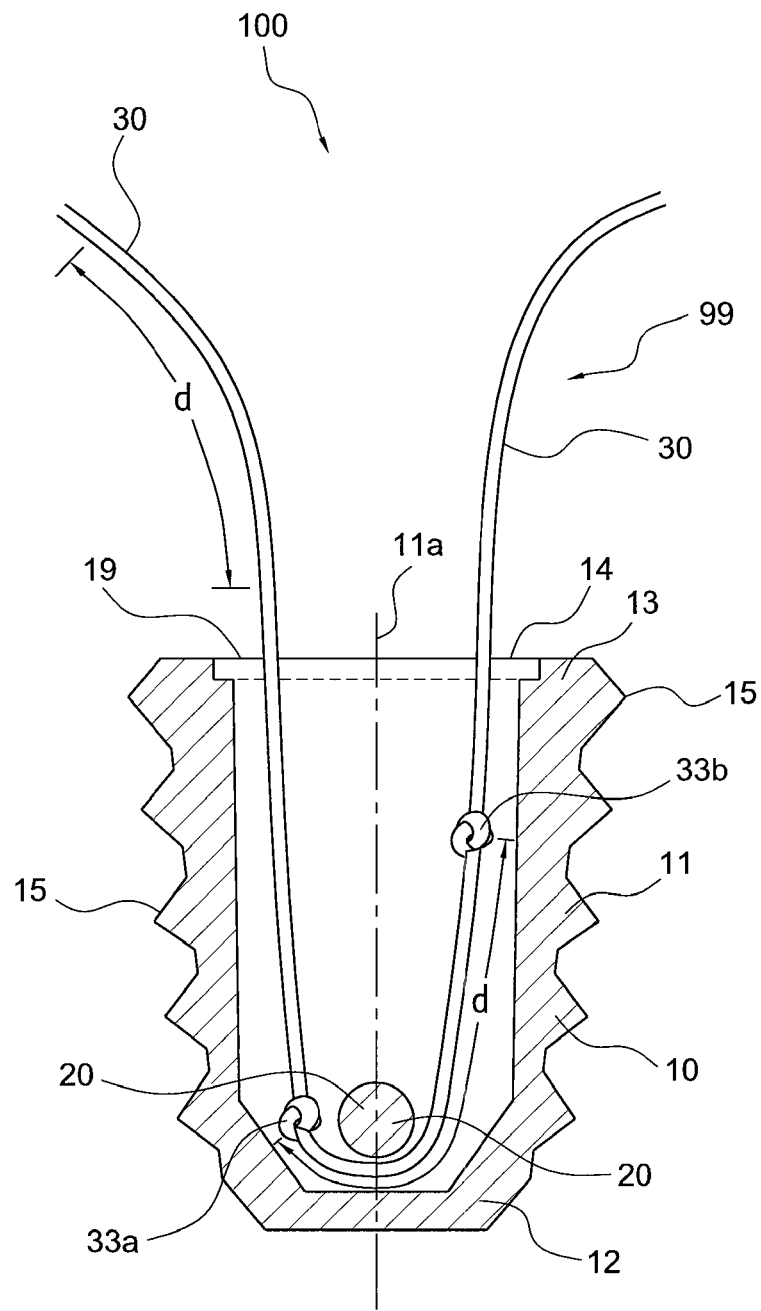
FIG. 1 illustrates a cross-sectional view of a fixation device according to an exemplary embodiment.

Surgical constructs, systems, and techniques for soft tissue repair and fixation, such as fixation of soft tissue (ligament, tendon, graft, etc.) to bone are disclosed.

A surgical construct is a single or double knot suture anchor that has a post or cross-bar located in the interior of the anchor, and a single suture strand passes into the anchor, around the post, and back out of the anchor. The suture strand has (i) one knot or stopper on one side of the anchor post, or (ii) two knots or stoppers, one on either side of the anchor post, that prevent the suture strand from moving too far in one or both directions.

A method of using a surgical construct (a suture anchor with a post located in the interior of the anchor, and a single suture strand passing into the anchor, around the post, and back out of the anchor, the suture strand having (i) one knot or stopper on one side of the anchor post, or (ii) two knots or stoppers, one on either side of the post, that prevent the suture strand from moving too far in one or both directions) comprises: inserting the anchor into bone, passing both suture limbs through tissue, tensioning the first suture limb such that the first knot or stopper is pulled towards the anchor post until the first knot or stopper stops at the anchor post, fixing the first suture limb to a second anchor, tensioning the second suture limb such that the first knot is pulled away from the anchor post, and fixing the second suture limb to a third anchor. In an embodiment having two knots or stoppers, tensioning the first suture limb pulls the second knot or stopper towards the anchor post until the second knot or stopper stops at the anchor post, and tensioning the second suture limb pulls the first knot or stopper towards the anchor post and the second knot or stopper away from the anchor post. This method allows for balanced tension between the two suture limbs.

A surgical construct includes a fixation device (a suture anchor) with a flexible strand (a suture) provided within the fixation device and around a post located within a body of the fixation device and at a distal end of the fixation device. A flexible strand may include one or two knots or similar structures (such as stoppers, stop members, protrusions, protuberances, beads, spheres, inserts, splices, tags, etc.) that are located on one or both sides of the post and prevent the flexible strand from moving too far in one or both directions. In an embodiment, the one or two knots or similar structures are fixedly located on (attached to) the flexible strand. In an embodiment, the one or two knots or similar structures are sized to be too large to pass around the post. A surgical construct may be inserted into bone and then limbs of the flexible strand are employed to approximate tissue to bone and achieve desired tension of the repair.

In an illustrative embodiment, a surgical construct comprises a fixation device with a body, a proximal end, a distal end, a longitudinal axis, a post located at the distal end of the body, and a flexible strand extending through a cannulation of the body and around the post. A flexible strand may include a plurality of stoppers or members that confer limited sliding ability to the flexible strand in at least one direction and relative to a fixed structure such as an anchor post. In an embodiment, two stoppers are provided within the body of a fixation device, each on either side of a post. The two stoppers are provided on the flexible strand, at a distance "d" between each other on the flexible strand. A flexible strand may slide only a distance "d." The two stoppers may be any knots, protrusions, protuberances, beads, spheres, splices, inserts, tags, or combination of these structures that allow limited sliding of a flexible strand relative to a fixed structure such as an anchor post. The two stoppers may be sized to be large enough to prevent passing of the stoppers around the post.

Methods of soft tissue repair which allow adjustment of both the tension of the suture and the location of the tissue with respect to the bone are also disclosed. An exemplary method comprises inter alia: (i) inserting a surgical construct into bone, the surgical construct comprising a fixation device (for example, an anchor), a post, and a flexible strand (for example, suture or filament) extending through the body and around the post of the fixation device, the flexible strand having two stoppers or similar structures attached to the flexible strand, each on either side of the post; (ii) passing limbs of the flexible strand around or through tissue to be fixated or reattached to bone, and pulling on each of the limbs (until at least one of the stopper opposite the limb that is being pulled contacts the post) to allow the soft tissue to achieve the desired location relative to the bone, and allow proper tensioning of the final construct; and (iii) securing the limbs to additional fixation devices. In an embodiment, the stoppers may be any structural member that confers limited sliding to the flexible strand and the limbs. The stoppers may be selected from the group consisting of knots, beads, spheres, splices, protrusions, protuberances, inserts, tags, or any larger diameter structure (provided on, within, or partially on the flexible strand) that is sized to be too large to permit sliding of the stoppers around the post (or around an anchor structure similar to the post).

In another embodiment, a method of tissue repair comprises: (i) securing a surgical construct into bone, the surgical construct comprising a fixation device (for example, a suture anchor), a post, and a suture strand extending through the body and around the post of the fixation device, the suture strand having two knots attached to the flexible strand, each on either side of the post; (ii) passing first and second suture limbs around or through tissue to be fixated (or reattached) to bone; (iii) pulling on first limb (until the second knot contacts the post) to allow the soft tissue to achieve a desired location relative to the bone, and then securing the first limb to a first fixation device; and (iv) pulling on the second limb to allow the suture strand to slip to further tension the construct and achieve balanced tension between the first and second suture limbs, and then securing the second limb to a second fixation device. In an embodiment, the knots are non-sliding static knots. In an embodiment, the first and second fixation devices are knotless fixation devices, which may be similar or different.

In another embodiment, the method of tissue repair comprises: (i) securing a surgical construct into bone, the surgical construct comprising a fixation device (for example, a suture anchor), a post, and a suture strand extending through the body and around the post of the fixation device, the suture strand having one knot attached to the flexible strand, located on one side of the post; (ii) passing first and second suture limbs around or through tissue to be fixated (or reattached) to bone; (iii) pulling on first limb (until the knot contacts the post) to allow the soft tissue to achieve a desired location relative to the bone, and then securing the first limb to a first fixation device; and (iv) pulling on the second limb to allow the suture strand to slip to further tension the construct and achieve balanced tension between the first and second suture limbs, and then securing the second limb to a second fixation device. In an embodiment, the knot is a non-sliding static knot. In an embodiment, the first and second fixation devices are knotless fixation devices, which may be similar or different.

Referring now to the drawings, where like elements are designated by like reference numerals, FIGS. 1-8 illustrate exemplary surgical constructs 100, 100a, and tissue repairs 200, 200a.

Surgical construct 100 of FIGS. 1-4 is formed of fixation device 10 assembled with construct 99 (tensionable construct 99) formed of flexible strand or flexible material 30 (suture 30) and two stop members 33a, 33b attached to the flexible strand 30. In particular and exemplary embodiments, the flexible strand 30 is a suture strand 30 and the stop members are knots 33a, 33b. In an exemplary embodiment, fixation device 10 is a tensionable anchor 10 provided with flexible strand 30 passing through the body of the tensionable anchor 10 and with stop members 33a, 33b attached to the flexible strand 30, each on each side of post or cross-bar 20.

In an exemplary embodiment, fixation device 10 is in the form of an anchor 10 having an anchor body 11 provided with a longitudinal axis 11a, a proximal end 13, and a distal end 12. A plurality of ribs, ridges or threads 15 may extend circumferentially around at least a part of anchor body 11. Cannulation 11b may be provided within anchor body 11 and extends along the body 11, as shown in FIG. 1, to allow one or more flexible strands 30 to pass therethrough, as detailed below. Post 20 in the form of an exemplary transversal bar is provided at distal end 12 of anchor body 11 to penult only limited sliding of flexible strand 30 around post 20, as also detailed below. Post 20 (bar or cross-bar 20) may be integral with anchor body 11 and may be provided in a direction about perpendicular to the longitudinal axis 11a, or may form angles other than 90 degrees angles with the longitudinal axis 11a.

Flexible strand 30 may be a suture strand or any suture-like material known in the art that could pass through tissue. Flexible strand 30 includes a plurality of stop members or stoppers 33a, 33b that confer limited sliding ability to the flexible strand 30 in at least one direction and relative to a fixed structure such as anchor post 20. In an embodiment, two stoppers 33a, 33b are provided within the body of a fixation device, each on either side of a post. The two stoppers 33a, 33b are provided on the flexible strand 30, a distance "d" from each other on the flexible strand. A flexible strand 30 may slide only a distance "d." The two stoppers 33a, 33b may be any knots, protrusions, protuberances, beads, spheres, splices, inserts, tags, or combination of these structures that allow limited sliding of a flexible strand 30 relative to a fixed structure such as an anchor post 20. The two stoppers 33a, 33b may be sized to be large enough to prevent passing of the stoppers around the post 20 (i.e., within a channel formed by post 20 and most distal end of the anchor body 11), and as detailed below.

In an exemplary embodiment, stoppers 33a, 33b are two suture knots 33a, 33b that are fixedly attached to flexible strand 30 and spaced apart a distance "d" from each other. The knots may be sliding knots or static knots. In an embodiment, the two knots are static knots fixedly located on (attached to) the flexible strand. In an embodiment, the two knots 33a, 33b are sized to be too large to pass around post 20. As detailed below, once anchor 10 is inserted into bone, limbs of flexible strand 30 are employed to approximate tissue to bone and achieve desired tension of the repair. By pulling one of the limbs (a first limb) in a first direction, the knots 33a, 33b prevent sliding of the flexible strand 30 for a distance greater than distance "d" as knot 33b contacts anchor post 20 (and stops at the anchor post 20), preventing further sliding/movement of the flexible strand 30 in the first direction. By pulling the other of the limbs (a second limb) in a second direction, the knots 33a, 33b prevent sliding of the flexible strand 30 for a distance greater than distance "d" as knot 33a could contact the anchor post 20 (and stop at the anchor post 20), preventing further sliding/movement of the flexible strand 30 in the second direction.

Cylindrical portion 14 may be provided at the proximal end 13 of the anchor 10 and may contain a socket 19 configured to securely engage a tip of a driver. Socket 19 of the anchor 10 may have any shape adapted to receive a driver tip for tapping or screw-in style anchors.

Anchor 10 may be a screw-in anchor or a push-in style anchor. Anchor 10 may be formed of metals, metal alloys, biocompatible plastics such as PEEK, or a bioabsorbable material such as PLLA material. Socket 19 at the distal end 13 of the anchor 10 is configured to securely engage a tip of a driver, as detailed below. Anchor 10 may be made of one or more pieces, or may be provided as an integrated device.

Figure 2:
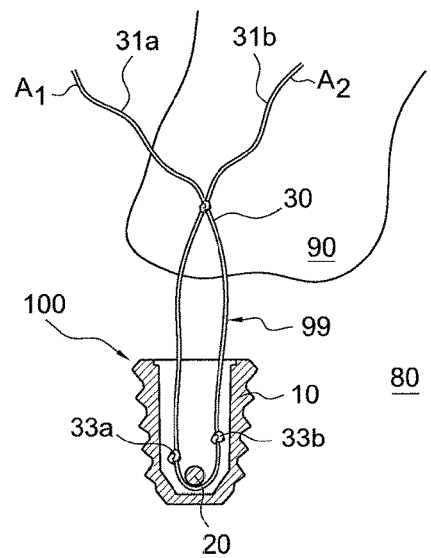
FIGS. 2-4 illustrate an exemplary method of tissue repair with the fixation device of FIG. 1.
Figure 3:
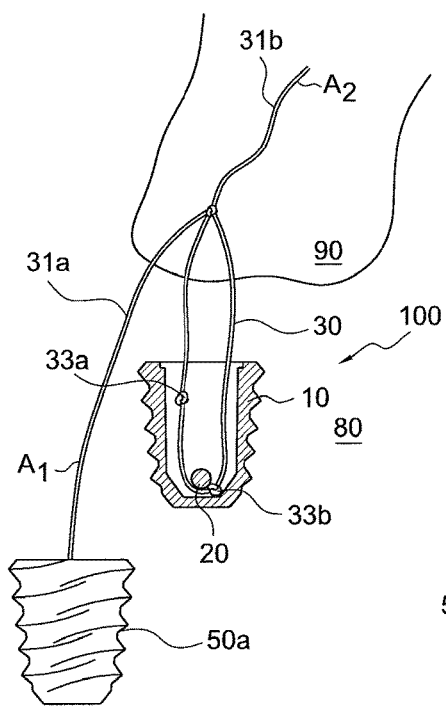
Figure 4:
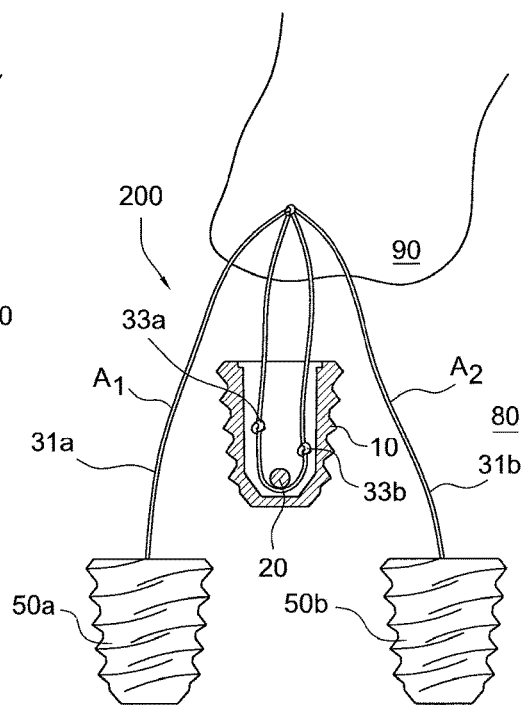

Reference is now made to FIGS. 2-4 which illustrate surgical construct 100 of FIG. 1 employed in a method of tissue repair, for example, soft tissue to bone repair.

FIG. 2 illustrates surgical construct 100 inserted into bone 80. Fixation device 10 (suture anchor 10) loaded with tensionable construct 99 (formed of suture 30 with two static suture knots 33a, 33b) is secured into bone 80 (for example, into a hole/socket/tunnel formed in the bone 80) by using a driver. The tensionable construct 99 may be formed by first passing flexible strand 30 through the cannulation 11b of the anchor body 11 and around the post 20, and then providing the two stop members 33a, 33b onto the flexible strand 30. In an exemplary embodiment, two suture static knots 33a, 33b are formed within the flexible strand 30 on each side of the post 20, so that the knots reside completely within the body 11 of the anchor 10. The knots may be formed by a surgeon or medical personnel by simply tying knots. If stop members 33a, 33b are in the form of beads or spheres, for example, a surgeon may assemble these structures onto flexible strand 30, subsequent to the step of passing the flexible strand 30 through the cannulation of the anchor body and around anchor post 20.

FIG. 2 depicts surgical construct 100 with fixation device 10 (anchor 10) after it has been inserted into a drilled hole in bone 80, the suture released from the driver, and the driver removed. Suture 30 is then passed through (or around) the tissue 90 which is to be reattached to bone. Specifically, limbs 31a, 31b (suture limbs 31, 31b or limbs A1, A2) of flexible strand 30 are passed through tissue 90. Limb 31a includes stop member 33a (static suture knot 33a). Limb 31b includes stop member 33b (static suture knot 33b). Stop members 33a, 33b (suture knots 33a, 33b) are contained within body 11 of fixation device 10, and on each side of post 20.

FIG. 3: Suture limb 31a (suture end 31a or limb A1) is tensioned and suture knot 33b contacts the anchor post 20. Suture limb 31a (limb A1) is further tensioned to reduce the tissue to bone, i.e., to approximate soft tissue 90 to bone 80. Suture limb 31a (limb A1) is then fixed with fixation device 50a, for example, a knotless suture anchor 50a (Anchor 2).

FIG. 4: Suture limb 31b (suture end 31b or limb A2) is tensioned allowing the suture to slip. Suture limb 31b (limb A2) can be tensioned more than suture limb 31a (limb A1) further reducing the tissue 80 and having balanced tension between the two suture limbs 31a, 31b (limbs A1, A2). Suture limb 31b (limb A2) is fixed with fixation device 50b, for example, a knotless suture anchor 50b, to complete final repair 200. Fixation device 50a may be similar to or different from fixation device 50b. Once the desired tension and location is achieved, suture ends 31a, 31b may be clipped off to complete the soft tissue repair or fixation.

The surgical constructs and systems of the present disclosure are used in conjunction with any fixation devices which can allow a flexible strand and attached one or more stoppers or stop members to pass around a post of the fixation device, with the stoppers resting on one or both sides of the post, and to aid in tissue repairs such as attachment of soft tissue to bone.

An exemplary method of tissue repair comprises inter alia: (i) inserting a surgical construct 100 into bone 80, the surgical construct comprising a fixation device 10 (for example, an anchor), a post 20, and a flexible strand 30 (for example, suture or filament) extending through body 11 and around the post 20 of the fixation device 10, the flexible strand 30 having two stoppers 33a, 33b attached to the flexible strand 30, each stopper 33a, 33b being located on one side of the post 20; (ii) passing limbs 31a, 31b of the flexible strand 30 around or through tissue 90 to be fixated or reattached to bone 80; (iii) pulling on each of the limbs 31a, 31b (until the stopper located on the limb opposite the one that is being pulled contacts the post) to allow the tissue 90 to achieve a desired location relative to the bone 80, and allow proper tensioning; and (iv) securing the first and second limbs 31a, 31b into bone. In an embodiment, the stoppers may be any structural member that confers limited sliding to the flexible strand and the limbs. The stoppers may be selected from the group consisting of knots, beads, spheres, splices, protrusions, protuberances, inserts, tags, or any larger diameter structure (provided on, within, or partially on the flexible strand) that is sized to be too large to permit sliding of the stoppers around the post (or around an anchor structure similar to the post). In an embodiment, the first and second limbs 31a, 31b are secured to bone 80 with fixation devices 50a, 50b which may be knotless fixation devices.

In another embodiment, a method of approximating soft tissue to bone comprises: (i) securing a surgical construct 100 into bone 80, the surgical construct 100 comprising a fixation device 10 (for example, a suture anchor 10), a post 20, and a tensionable construct 99 formed of a suture strand 30 extending through the body and around the post of the fixation device, the suture strand 30 having two knots 33a, 33b attached to the flexible strand 30 and spaced apart from each other by a distance "d", each of the two knots being located on one side of the post 20 and opposite to each other relative to the post 20, so that a first suture limb 31a has a first knot 33a, and a second suture limb 31b has a second knot 33b; (ii) passing first and second suture limbs 31a, 31b through tissue 90 to be approximated (or reattached) to bone 80; (iii) pulling on first limb 31a until second knot 33b contacts post 20, to allow soft tissue 90 to achieve a first location relative to bone 80; (iv) securing the first limb 31a to a first fixation device 50a; (v) pulling second limb 31b to allow the suture strand 30 to slip to further tension the construct, to allow soft tissue 90 to achieve a second location relative to bone 80, and to achieve balanced tension between the first and second suture limbs 31a, 31 b; and (vi) securing the second limb 31b to a second fixation device 50b. In an embodiment, the knots are non-sliding suture knots, and the first and second fixation devices are knotless fixation devices.

FIGS. 5-8 depict surgical construct 100a, which is the same as surgical construct 100 of FIGS. 1-4, except that surgical construct 100a has only one stop member 33. In an exemplary embodiment, stop member 33 is provided on the flexible strand 30a. The flexible strand 30a may slide in one direction until the stopper 33 contacts post 20. The flexible strand 30a may slide in the opposite direction up to a length equal to the distance from stop member 33 to the end of flexible strand 30a. Like in the above-described embodiment, stop member 33 may be a knot, protrusion, protuberance, bead, sphere, splice, insert, tag, or combination of these structures that allow limited sliding of a flexible strand 30a relative to a fixed structure such as an anchor post 20. The stop member 33 may be sized to be large enough to prevent passing of the stop member around the post 20 (i.e., within a channel formed by post 20 and most distal end of the anchor body 11).

Figure 5:
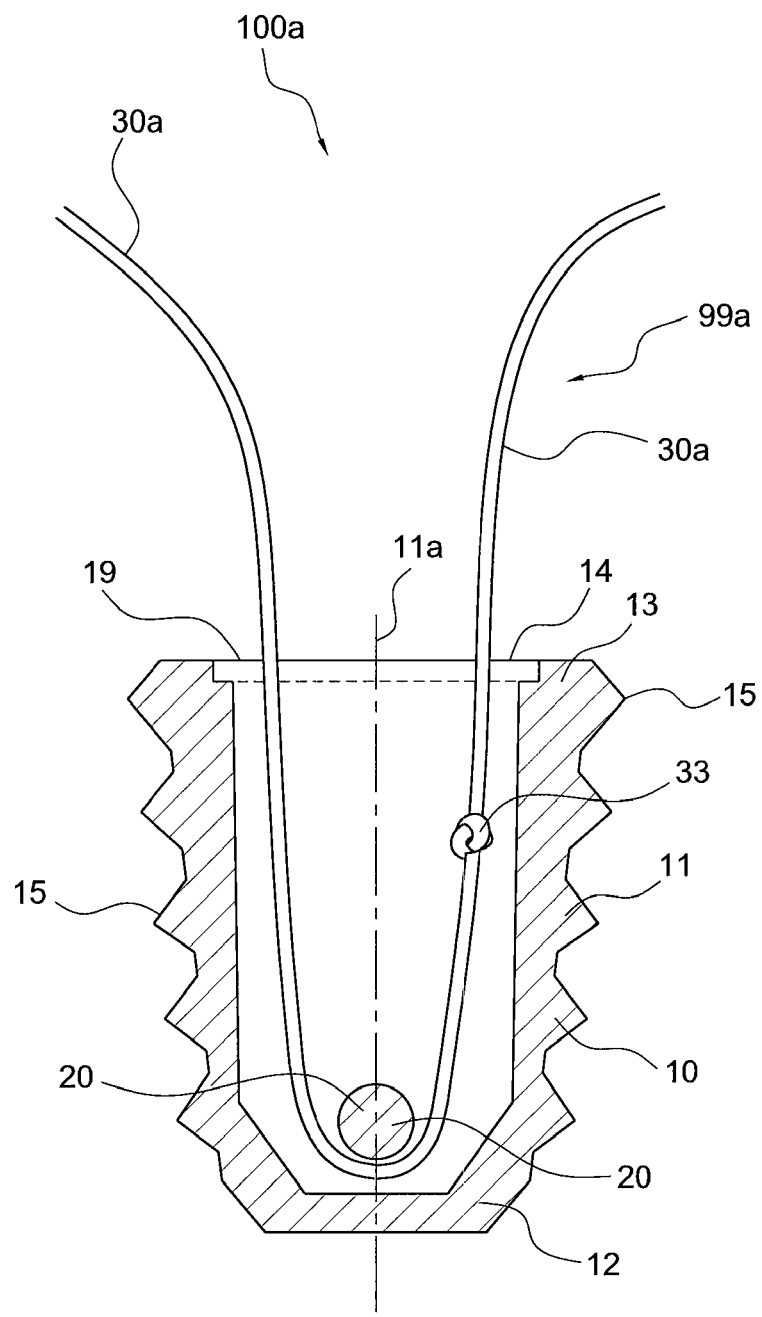
FIG. 5 illustrates a cross-sectional view of a fixation device having one knot or stopper, according to another exemplary embodiment.
Figure 6:
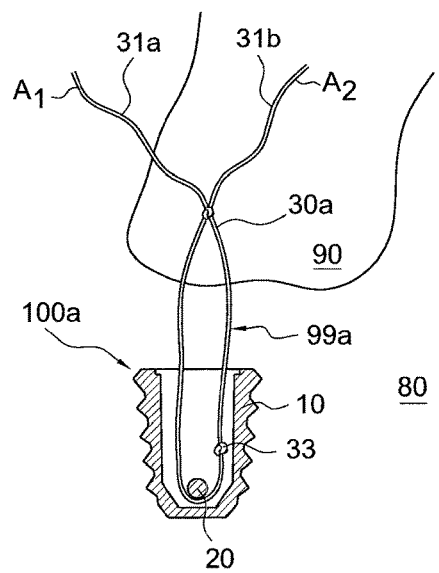
FIGS. 6-8 illustrate an exemplary method of tissue repair with the fixation device of FIG. 5.
Figures 7, 8:
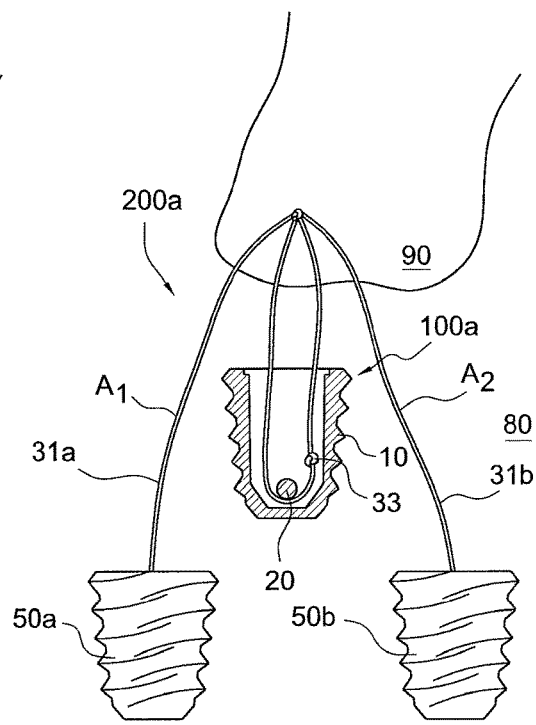

Reference is now made to FIGS. 6-8, which illustrate surgical construct 100a of FIG. 5 employed in a method of tissue repair, for example, soft tissue to bone repair.

FIG. 6 illustrates surgical construct 100a inserted into bone 80. Fixation device 10 (suture anchor 10) loaded with tensionable construct 99a (formed of flexible strand 30a with one static suture knot 33) is secured into bone 80 (for example, into a hole/socket/tunnel formed in the bone 80) by using a driver. The tensionable construct 99a may be formed by first passing flexible strand 30a through the cannulation 11b of the anchor body 11 and around the post 20, and then providing one stop member 33 onto the flexible strand 30a. In an exemplary embodiment, one suture static knot 33 is formed within the flexible strand 30a on one side of the post 20, so that the knot resides completely within the body 11 of the anchor 10. The knot may be formed by a surgeon or medical personnel by simply tying knots. If stop member 33 is in the form of a bead or sphere, for example, a surgeon may assemble these structures onto flexible strand 30a, subsequent to the step of passing the flexible strand 30a through the cannulation of the anchor body and around anchor post 20.

FIG. 6 depicts surgical construct 100a with fixation device 10 (anchor 10) after it has been inserted into a drilled hole in bone 80, the suture released from the driver, and the driver removed. Flexible strand 30a is then passed through (or around) the tissue 90 which is to be reattached to bone. Specifically, limbs 31a, 31b (suture limbs 31, 31b or limbs A1, A2) of flexible strand 30a are passed through tissue 90. Limb 31b includes stop member 33 (static suture knot 33). Stop member 33 is contained within body 11 of fixation device 10, and on one side of post 20.

FIG. 7: Suture limb 31a (suture end 31a or limb A1) is tensioned and suture knot 33 contacts the anchor post 20. Suture limb 31a (limb A1) is further tensioned to reduce the tissue to bone, i.e., to approximate soft tissue 90 to bone 80. Suture limb 31a (limb A1) is then fixed with fixation device 50a, for example, a knotless suture anchor 50a (Anchor 2).

FIG. 8: Suture limb 31b (suture end 31b or limb A2) is tensioned allowing the suture to slip. Suture limb 31b (limb A2) can be tensioned more than suture limb 31a (limb A1) further reducing the tissue 80 and having balanced tension between the two suture limbs 31a, 31b (limbs A1, A2). Suture limb 31b (limb A2) is fixed with fixation device 50b, for example, a knotless suture anchor 50b, to complete final repair 200a. Fixation device 50a may be similar to or different from fixation device 50b. Once the desired tension and location is achieved, suture ends 31a, 31b may be clipped off to complete the soft tissue repair or fixation.

An exemplary method of tissue repair comprises inter alia: (i) inserting a surgical construct 100a into bone 80, the surgical construct comprising a fixation device 10 (for example, an anchor), a post 20, and a flexible strand 30a (for example, suture or filament) extending through body 11 and around the post 20 of the fixation device 10, the flexible strand 30a having stopper 33 attached to the flexible strand 30a, stopper 33 being located on one side of the post 20; (ii) passing limbs 31a, 31b of the flexible strand 30a around or through tissue 90 to be fixated or reattached to bone 80; (iii) pulling on one of the limbs 31a, 31b (until the stopper 33 located on the limb opposite the one that is being pulled contacts the post) to allow the tissue 90 to achieve a desired location relative to the bone 80, and allow proper tensioning; and (iv) securing the first and second limbs 31a, 31b into bone. In an embodiment, the stopper may be any structural member that confers limited sliding to the flexible strand and the limbs. Stopper 33 may be selected from the group consisting of a knot, bead, sphere, splice, protrusion, protuberance, insert, tag, or any larger diameter structure (provided on, within, or partially on the flexible strand) that is sized to be too large to permit sliding of the stopper around the post (or around an anchor structure similar to the post). In an embodiment, the first and second limbs 31a, 31b are secured to bone 80 with fixation devices 50a, 50b which may be knotless fixation devices.

In another embodiment, a method of approximating soft tissue to bone comprises: (i) securing a surgical construct 100a into bone 80, the surgical construct 100a comprising a fixation device 10 (for example, a suture anchor 10), a post 20, and a tensionable construct 99a formed of a suture strand 30a extending through the body and around the post of the fixation device, the suture strand 30a having knot 33 attached to the flexible strand 30a and being located on one side of the post 20, so that a first suture limb 31a has no knot and a second suture limb 31b has knot 33; (ii) passing first and second suture limbs 31a, 31b through tissue 90 to be approximated (or reattached) to bone 80; (iii) pulling on first limb 31a until knot 33 contacts post 20, to allow soft tissue 90 to achieve a first location relative to bone 80; (iv) securing the first limb 31a to a first fixation device 50a; (v) pulling second limb 31b to allow the suture strand 30a to slip to further tension the construct, to allow soft tissue 90 to achieve a second location relative to bone 80, and to achieve balanced tension between the first and second suture limbs 31a, 31b; and (vi) securing the second limb 31b to a second fixation device 50b. In an embodiment, the knot is a non-sliding suture knot, and the first and second fixation devices are knotless fixation devices.

Fixation devices 50a, 50b may be any of swivel and/or screw-in suture anchors and/or push-in suture anchors (such as an Arthrex SwiveLock® anchor, disclosed in U.S. Patent Application Publication No. 2008/0004659 or a PushLock® anchor, as disclosed in U.S. Pat. No. 7,329,272). Fixation devices 50a, 50b may be also any anchors, implants or screws (such as interference screws or tenodesis screws) or any fixation element that allows attachment/fixation of the limbs of flexible strands 30, 30a to bone. The fixation devices/implants may have various sizes (various diameters and/or lengths) and may be formed of biocompatible materials such as PEEK, biocomposite materials, metals and/or metal alloys, or combination of such materials, among others.

Flexible strands 30, 30a may be a suture strand or any suture-like material known in the art that could pass through tissue and could be provided with stop members 33, 33a, 33b such as suture knots 33, 33a, 33b. Flexible strands 30, 30a may include a high-strength suture, such as an ultrahigh molecular weight polyethylene (UHMWPE) suture. High strength suture may be a FiberWire® suture (Arthrex). FiberWire® suture is formed of an advanced, high-strength fiber material, namely ultrahigh molecular weight polyethylene (UHMWPE), sold under the tradenames Spectra® (Honeywell International Inc., Colonial Heights, Va.) and Dyneema® (DSM N.V., Heerlen, the Netherlands), braided with at least one other fiber, natural or synthetic, to form lengths of suture material.

Flexible strands 30, 30a may be also formed of a stiff material, or combination of stiff and flexible materials, depending on the intended application. The strand may be also coated and/or provided in different colors. Flexible strands 30, 30a may be provided with a uniform diameter (with the exception of the one or two regions on which stop members 33, 33a, and 33b are provided) or with various diameters provided on different lengths of the strand.

What is claimed is:

1. A surgical construct for tissue repairs, comprising:
  a fixation device comprising a body, a longitudinal axis, a proximal end, a distal end, a post located at the distal end, at least a portion of the body being cannulated; and
  a tensionable construct pre-loaded on the fixation device, the tensionable construct comprising a flexible strand and two stop members attached to the flexible strand, the tensionable construct extending through the body of the fixation device, the two stop members being positioned each on either side of the post and statically spaced apart from one another, at least one of the two stop members is located within the body of the fixation device and is sized to abut the post when the tensionable construct is tensioned, thereby limiting sliding of the flexible strand through the body of the fixation device.

2. The surgical construct of claim 1, wherein the post extends in a direction about transversal to the longitudinal axis of the body, and wherein the two stop members allow limited sliding of the flexible strand through the body of the fixation device and around the post.

3. The surgical construct of claim 1, wherein the flexible strand is a suture formed of ultrahigh molecular weight polyethylene.

4. The surgical construct of claim 1, wherein the two stop members are selected from the group consisting of knots, protrusions, protuberances, beads, spheres, inserts, splices and tags.

5. The surgical construct of claim 1, wherein the two stop members comprise suture knots.

6. The surgical construct of claim 1, wherein the fixation device is an anchor with an anchor body provided with a plurality of circumferential ribs extending from an outer surface of the anchor body.

7. The surgical construct of claim 1, wherein both of the two stop members are located within the body of the fixation device.

8. The surgical construct of claim 1, wherein the at least one stop member has at least one dimension that is larger than a channel defined between the post and the body of the fixation device.

9. The surgical construct of claim 1, wherein the other of the two stop members is attached to the flexible strand spaced from the at least one stop member to define a sliding distance therebetween, wherein sliding of the flexible strand through the body of the fixation device for a distance greater than the sliding distance is prevented.

10. The surgical construct of claim 1, wherein the flexible strand is a suture having at least one limb, the limb being configured to be fixed to another fixation device.

* * * * *